Patented June 23, 1936

Plant Pat. 186

UNITED STATES PATENT OFFICE

186

PEACH

Charles Edward Sullivan, Yuba City, Calif.

No Drawing. Application November 9, 1935, Serial No. 49,118

1 Claim. (Cl. 47—62)

This invention or discovery relates in general to peaches, and is directed in particular to a peach tree and its fruit of the yellow fleshed cling type.

The peach tree herein described was discovered in March, 1928 on my ranch in Sutter County, California, as a sprout from a seedling understock on which the Phillips variety was budded and since its discovery I have successfully asexually reproduced the same. As yet this peach tree has not been grown other than in Sutter County, California, but some 836 trees of this variety other than the parent tree, have been grown and found to have the qualities hereinafter described.

My new peach is of especial commercial value due to the fact that the tree is hardy with good resistance to insects and disease and in particular the foliage and bark are practically immune to scale. The fruit of the tree does not gum, is practically free from reddening at the pit, oxidizes slowly when peeled or cut open, and ripens approximately five days earlier than the Phillips cling peach.

The following description sets forth in detail the characteristics of my improved peach tree and its fruit.

*Tree.*—The tree is hardy and large, a vigorous grower, upright, dense, vase formed, very productive, and a regular bearer. The trunk of the tree is stocky and the bark is shaggy. The main branches are stocky, of medium smoothness, brown in color, have numerous lenticels, and the fruit wood is attached to the main branches and droops from them towards the ground.

*Leaves.*—The leaves are thick and large averaging 6¼ inches in length and 1½ inches in width and are bluish green in color differentiating them from the bright or sallow green leaves of other similar varieties of peaches. The leaves are lanceolate, acutely pointed, rugose, the margin is finely serrate, the petiole is long and of medium size, and each leaf has an average of four alternate large red reniform glands at the base of the leaf on the stem. Stipules are wanting.

*Flower buds and flowers.*—The flower buds are hardy, of medium size, long, plump, free, pubescent. The flowers bloom on the average from February 28 to March 10 and are of medium size and pink color.

*Fruit.*—The fruit is large, uniform, and averages 2⅝ inches in diameter axially, 3⅜ inches transversely in the suture plane, and 3⅜ inches transversely at right angles to the suture plane. In form the fruit is uniform, symmetrical, globose, oblate, and compressed transversely toward suture. The suture is distinct, shallow, and extends from the base to the apex but does not extend beyond the pistil point. The ventral surface is rounded slightly, lipped towards base on both sides, and the lips are equal. Cavity is ½ inch deep and 1½ inches in breadth, rounded elongated in suture plane with suture showing on one side and there are no markings. Base is truncate and apex is short and rounded to truncate. Pistil point is apical. The stem is stout, glabrous, adheres strongly to stone, and averages ⅜ inch in length. The skin of the fruit is medium, tough, tenacious to flesh, and has only a slight tendency to crack and then only in the dry season. The skin is yellow with a red blush, and there is moderate down medium in length which does not roll up when rubbed. The flesh is yellowish, the surface of the pit cavity is yellow, and there is no reddening at the pit as in the Halford peach.

The juice of the fruit is moderate in quantity and rich. Amygdalin is wanting. The texture of the flesh is firm and meaty, fibers are few and tender, flavor is delicate, aroma is pronounced, the fruit ripens even, and is of the best eating quality. In appearance and character the fruit may be said to be midway between the Sims and the Gaume possessing some of the good qualities of each.

*Stone.*—The stone clings, adheres to flesh over entire surface, is small averaging 1⅜ inches in length, 1⅛ inches in breadth, and ¾ inch in thickness, cuneate toward base and apex, base is straight, hilum is oblong and apex is acuminate. The sides of the stone are equal and the surface is regularly furrowed and ridged throughout. Ridges are rounded, the ventral edge is thick without wing, and the dorsal edge is full, shallow throughout and ridges on either side are interrupted. The stone is brown in color and has but slight tendency to split.

*Ripening period.*—The peach described herein ripens approximately five days earlier than the Phillips cling peach, picking beginning usually on August 30 and continuing until September 12.

*Use.*—This peach is used essentially for canning and due to its novel characteristics is especially suitable for that purpose. Its keeping and shipping qualities are good.

The principal characteristics of my new peach which I believe to be novel and distinguish it from the Phillips cling peach and other similar varieties are as follows:

The bark of the tree and the foliage have strong resistance to scale, the fruit does not gum and is practically free from reddening at the pit; oxidizes slowly when peeled or cut open, and ripens approximately five days earlier than the Phillips cling peach.

The above described characteristics are of course typical and may be subject to certain variations as all varieties of fruit differ among themselves in adaption to a particular region, soil, or climatic conditions.

Having thus described my invention, what I claim as new and useful and desire to secure by Letters Patent is:

The herein described peach tree characterized by its strong resistance to insects and disease, and by the lack of gumming of the fruit, its freedom from reddening at the pit, resistance to oxidization when peeled or cut, as compared to the Phillips cling peach, and ripening approximately five days earlier.

CHARLES EDWARD SULLIVAN.